United States Patent [19]

Mobley

[11] Patent Number: 5,039,707

[45] Date of Patent: Aug. 13, 1991

[54] 1,3,6,8 TETRAHYDROXYANTHRAQUINONE

[76] Inventor: James R. Mobley, 4391 Deerwood La., Evans, Ga. 30809

[21] Appl. No.: 404,583

[22] Filed: Sep. 8, 1989

[51] Int. Cl.$^5$ .................. A61K 31/12; C07C 50/18
[52] U.S. Cl. .................... 514/680; 514/892; 552/261
[58] Field of Search .......... 552/261, 262, 228; 514/680, 892

[56] References Cited

U.S. PATENT DOCUMENTS

| | | | |
|---|---|---|---|
| 772,857 | 10/1904 | Wolman | 552/261 |
| 871,507 | 11/1907 | Homolka et al. | 552/261 |
| 1,586,039 | 5/1926 | Impens | 514/680 |
| 3,773,801 | 11/1973 | Lang | 552/261 |
| 4,739,062 | 4/1988 | Bigi et al. | 552/262 |

FOREIGN PATENT DOCUMENTS 3315463  10/1984  Fed. Rep. of Germany ...... 514/680

OTHER PUBLICATIONS

Chemical Abstracts vol. 94, #153097c, 1981, Yves, "1,3,6,8-Tetrahydroxyanthraquinone".

Primary Examiner—Richard L. Raymond
Assistant Examiner—Raymond Covington

[57] ABSTRACT

A method for causing laxation using 1, 3, 6, 8-tetrahydroxyanthraquinone.

1 Claim, No Drawings

1,3,6,8 TETRAHYDROXYANTHRAQUINONE

SUMMARY OF THE INVENTION

The substance is a synthetically produced, non naturally occurring chemical. It is intended for medical use. Principally 1, 3, 6, 8 Tetrahydroxyanthraquinone is a laxative acting as a stimulant to the meuromuscular junction of the bowel wall.

DETAILED DESCRIPTION

The manufacture of 1, 3, 6, 8 Tetrahydroxyanthraquinone is accomplished by a process described below. A naturally occurring plant product, 1, 3, 8 Trihydroxymethylanthraquinone Glycosilate, is the easiest starting point for manufacture and and is the natural substance most like our intended patent substance. This substance has been found in a variety of plants from fungi to rhubarb. The most common source is Cascara Sagrada which has been used medically as a laxative for hundreds of years. The most advantageous difference between the natural substance, Cascara Sagrada, and 1, 3, 6, 8 Tetrahydroxyanthraquinone is that the substance to be patented does not require metabolism by intestinal bacteria before it can be absorbed and used by the body. This yields two distinct areas of superiority. It can be given directly by injection and the onset of action is much faster. Both results are achieved because the active component does not require time to travel in the gut, or change by gut bacteria.

The manufacture of Tetrahydroxyanthraquinone begins with the removal of the sugar moiety from 1, 3, 8 Trihydroxymethylanthraquinone glycosilate which leaves the following molecule:

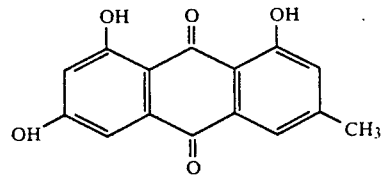

At this point the methyl group, CH3, is replaced with a halogen atom, usually fluorine, which is then substituted to a hydroxyl group yielding the final product.

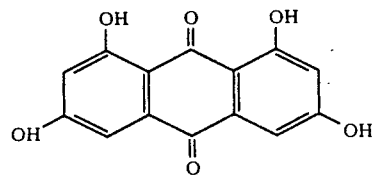

This sequence from the plant product is the simplest route to the production of 1, 3, 6, 8 Tetrahydroxyanthraquinone. It can be produced by any number of procedures joining three aromatic rings with double bonded oxygen attached at the available sites on the central ring and hydroxyl groups attached at the 1 and 3 positions of each outer ring making a symmetrical molecule. In this patent is also claimed any similar process which leads to the production of 1, 3, 6, 8 Tetrahydroxyanthraquinone. A variety of chemicals are reasonable starting points for the production of 1, 3, 6, 8 Tetrahydroxyanthraquinone such as the antibiotic Tetracycline; however, starting with the plant product 1, 3, 8 Trihydroxymethylanthraquinone Glycosilate is the most efficient way to produce 1, 3, 6, 8 Tetrahydroxyanthraquinone.

I claim:

1. A method for producing a laxative effect in a body which comprises administering thereto 1, 3, 6, 8 tetrahydroxyanthraquinone to stimulate the neuromuscular junction of the bowel wall.

* * * * *